(12) United States Patent
Verly et al.

(10) Patent No.: US 10,457,144 B2
(45) Date of Patent: Oct. 29, 2019

(54) REAL TIME PREDICTION DEVICE

(71) Applicant: Université de Liège, Angleur (BE)

(72) Inventors: Jacques Verly, Angleur (BE); Pouyan Ebrahimbabaie, Liège (BE)

(73) Assignee: UNIVERSITÉDE LIÈGE, Angleur (BE)

(*) Notice: Subject to any disclaimer, the term of this patent is extended or adjusted under 35 U.S.C. 154(b) by 23 days.

(21) Appl. No.: 15/747,806

(22) PCT Filed: Jul. 22, 2016

(86) PCT No.: PCT/EP2016/067508
§ 371 (c)(1),
(2) Date: Jan. 26, 2018

(87) PCT Pub. No.: WO2017/029068
PCT Pub. Date: Feb. 23, 2017

(65) Prior Publication Data
US 2018/0215262 A1     Aug. 2, 2018

(30) Foreign Application Priority Data
Aug. 14, 2015  (EP) .................................... 15181180

(51) Int. Cl.
*B60K 28/06* (2006.01)
*G06N 7/00* (2006.01)
*A61B 5/18* (2006.01)
*A61B 5/00* (2006.01)

(52) U.S. Cl.
CPC .......... *B60K 28/066* (2013.01); *G06N 7/005* (2013.01); *A61B 5/18* (2013.01); *A61B 5/7264* (2013.01); *B60K 28/06* (2013.01)

(58) Field of Classification Search
None
See application file for complete search history.

(56) References Cited

U.S. PATENT DOCUMENTS

| | | | |
|---|---|---|---|
| 2004/0236235 A1 | 11/2004 | Fujita et al. | |
| 2010/0245093 A1* | 9/2010 | Kobetski | A61B 5/18 340/576 |
| 2014/0152792 A1* | 6/2014 | Krueger | A61M 21/00 348/78 |

(Continued)

OTHER PUBLICATIONS

G. Yang et al., A driver fatigue recognition model based on information fusion and dynamic Bayseian network, (Jan. 2010), Information Sciences 180, 1942-1954.*

(Continued)

*Primary Examiner* — Thomas S McCormack
(74) *Attorney, Agent, or Firm* — Jacobson Holman, PLLC.

(57) ABSTRACT

The invention is directed to a prediction device for use in combination with a human being where the human being issues data. The prediction device comprises
a means to acquire the data from inside or outside the human being for one or more time periods located in a time interval from a moment in the past to the present moment to obtain an acquired data set,
a means to model the acquired data set as a geometric Brownian motion random process model to obtain a fitted random process model, and
a means to predict a state of the human being using the fitted random process model to obtain a predicted state of the human being.

20 Claims, 13 Drawing Sheets

(56) References Cited

U.S. PATENT DOCUMENTS

2015/0169840 A1* 6/2015 Kupfer .................. G16H 50/30 702/19

OTHER PUBLICATIONS

International Search Report, dated Oct. 13, 2016 (3 pages).
Yang G. et al., "A driver fatigue recognition model based on information fusion and dynamic Bayesian network", *Information Sciences*, vol. 180, n° 10, 2010, pp. 1942-1954, cited in the ISR.
Commenges et al., "Evidence synthesis through a degradation model applied to myocardial infarction", *Lifetime data analysis, an International Journal devoted to statistical methods and applications for time-t-event data*, vol. 19, n° 1, 2012, pp. 1-18, cited in the ISR.
Punjabi et al., "Modeling hypersomnolence in sleep-disordered breathing a novel approach using survival analysis", American Journal of Respiratory and Critical Care Medicine, vol. 159, n° 6, 1999, pp. 1703-1709, cited in the ISR.
Li et al., "Estimation of eye closure degree using EEG sensors and its application in driver drowsiness detection", Sensors, vol. 14, n° 9, 2014, pp. 17491-17515, cited in the ISR.
Jeanblanc, M. Mathematical Methods for financial markets, 2009, pp. 38-45.
David G. Kleinbaum, Survival Analysis, 2005, pp. 4-14.
Dong et al., "Driver Inattention Monitoring System for Intelligent Vehicles: A Review", IEEE Transactions on Intelligent Transportation Systems, vol. 12, No. 2, Jun. 6, 2011, pp. 596-614, cited in the ISR.
V. Nair et al., "Stochastic Processes in Survival Analysis", Advances in Statistical Modeling and Inference, Jan. 14, 2005, abstract only, cited in the ISR.

\* cited by examiner

REAL TIME PREDICTION DEVICE

BACKGROUND OF THE INVENTION

The invention is directed to a real time prediction device for use in combination with a human being where the human being issues data.

In many applications there is an interest in producing one or more alarms based on the state of a human being, where the human being issues data, which can typically be acquired via appropriate sensors. Following capture, the data is generally transformed in some sort of a signal, typically electronic. One or more such signals may then be combined into other signals that are not directly generated by the human being. These signals are typically obtained by computation but are related to the data issued by the human being.

An example of such an application is a device to prevent a driver of a vehicle from falling asleep at the wheel or from having an accident due to drowsiness or, equivalently, to somnolence. Here, the driver is obviously the human being of interest. The signal related to the data might be a level of drowsiness of the driver obtained in some way, e.g. via polysomnography (PSG) or via photooculography (POG). The device would issue an alarm when the level of drowsiness reaches a level deemed "reference level". The alarm may be, among others, by audible, visible, olfactory, and/or vibratory means.

US2004/0236235 describes a human condition detection system for detecting the transition from an active sate to a sleep state. A bio-signal analysis means includes a bio-signal peak value detection means for detecting a peak value for each cycle of an original waveform of bio-signal data, and a power value calculation means for calculating a difference between the peak value at an upper limit side and the peak value at a lower limit side for every prescribed time range. A slide calculation is performed to determine if a sudden drop state appears that is indicative of falling asleep. This publication predicts the human condition at the present moment.

While it is obviously important to be able to determine the level of drowsiness of a driver and to make predictions about this level in the case of conventional vehicles and driving, it is also important to do so in the case of self-driving vehicles. Indeed, the automatic driving system may decide to take over from the driver if it determines that the level of drowsiness of the driver becomes too high, or the automatic driving system may need to decide whether it is safe to hand over the "manual" driving to the driver.

In the field of predicting a future state based on past events, one often assumes that the input, i.e. the data as issued by the human being, is a realization of a moving average (MA) random process, or an autoregressive (AR) random process, or an autoregressive moving average (ARMA) random process, or similar traditional random processes. Equivalently, one can say that the input is modeled by an MA, AR random process, or ARMA random process. These techniques allow one to estimate the future values of a signal as linear combinations of previous (and known) values of the signal, typically in a window. The prediction process is then implemented via a linear-time invariant (LTI) system.

Two disadvantages of such methods is that the MA, AR, and ARMA random process models may not be accurate for the application of interest and/or that they usually require significant computational capability in actual use as further described below.

BRIEF SUMMARY OF THE INVENTION

The present invention is directed to an improved prediction device of the state of a human being, as described below, and which may for example find application in combination with an alarm.

A real time prediction device comprising a means to acquire data from inside or outside a human being for one or more time periods in the past to obtain an acquired data set, wherein the data is a level of drowsiness or an ocular parameter indicative for drowsiness, a computer means configured to model the acquired data set as a geometric Brownian motion (GBM) random process model or an Ito process (IP) random process model to obtain a fitted random process model, and a computer means configured to predict in real time a state of drowsiness of the human being using the fitted random process model to obtain a predicted state of drowsiness of the human being.

Applicant found that, when a geometric Brownian motion (GBM) random process model or an Ito process (IP) random process model is used to model the data, a good prediction of the state of drowsiness of the human being can be obtained as further described below.

The random process model is a geometric Brownian motion (GBM) random process model. Geometric Brownian motion (GBM) random process models are well known and for example described by Jeanblanc, M. (2009), Mathematical Methods for Financial Markets (pp. 38-45), London: Springer. The acquired data set or sets and especially in the field of drowsiness are found to be realizations of GBM random processes. The computer means configured to model the acquired data set suitably comprises a means configured to calculate one or more parameters of the random process model using the acquired data set as input.

The acquired data set may comprise one or more of each of a temporal signal or spatial-temporal signal for one or more time periods located in a time interval comprised from a moment in the past to the present moment, i.e. for one or more time periods in the past. The acquired data sets of interest are generally signals of time, or temporal signals, i.e. signals the amplitudes of which vary with time. Continuous time is generally represented by the continuous variable t, and discrete time by the discrete/integer variable/index n. The amplitude is generically designated by x. Hence, the input signal of interest is denoted by x(t) or x[n]. In the present description, the acquired data set or signal is considered to be of continuous time, this without any loss of generality. In practice, i.e. in digital systems, one generally uses discrete time data sets or signals.

Because the invention is directed to a device suited for real time prediction, there will, at a certain time, always be a past, a present moment, and a time in the future. Throughout the present description, the person skilled in the art will have no difficulty distinguishing between random processes or models and their realizations, even if they are designated by the same notation, such as x(t) or x[n], and this person will have no difficulty determining whether the expressions and notations refer to the part(s) of x(t) or x[n] corresponding to the past, present, and/or future.

Suitably only part of the available acquired data set is used, suitably over a specified duration ending at the present time (i.e. "now" or "present moment"). In other words, one only considers the portion of the acquired data set that is located within a "window" of time, or sometimes referred to as a windowed signal. Such a window will slide over the time axis, typically to ensure that its right end always corresponds to the present time. When making predictions, the notions of present, past, and future are important. The acquired data set or signal, denoted by x(t), is only known up to the present, i.e. for the past and the present. In other words, and of course, the acquired data set or signal is not known for the future. Said differently, the data or signal is known for the past and present and unknown for the future. Making predictions about the future is precisely the main objective of the prediction device according to the present invention.

The means to acquire the acquired data sets or signals for a time period may be sensors or any other means to acquire such signals. For example, in a device that is suited to predict drowsiness (or somnolence), the acquired data set may be the variation with time of the level of drowsiness (or somnolence), or the variations with time of the value of an ocular parameter indicative of drowsiness, such as the PERCLOS (percentage closure) parameter, which is known to be indicative of drowsiness.

The device may comprise more than one means to predict the state of the human being. In such a device, the acquired data set may be the same for each means. Furthermore, the computer means configured to model the acquired data set as a geometric Brownian motion (GBM) random process model or an Ito process (IP) random process model to obtain a fitted random process model and the computer means configured to predict the state of the human being using the fitted random process model to obtain a predicted state of the human being may be the same or different for each means to predict. The predicted state of the human being of a single means in case of one means or each means separately in case of more than one means can be fed as such to an alarm system. More than one predicted state of the human being may also be combined into a combined predicted state of the human being by combining these means before being fed to the alarm system.

In this description, the term "reference level" will be used. The "reference level" and the data as issued by the human being (x(t)) will preferably have the same amplitude scale, for example in volts or meters, or without units on some arbitrary scale, such as for a level of drowsiness. The reference level is a specified value and is linked to some sort of action.

A next important term is that of "time of first hit" or, equivalently, "time to first hit" or "first hitting time", which is the time when the data set or signal x(t) first reaches the reference level. In general, one assumes that the signal x(t) starts below the reference level. While it would be possible to define a "time of first hit" if the signal was initially above the reference level, this may not be of interest in practice. Consider the following example. If x(t) represents the level of drowsiness of a driver and the goal is to prevent accidents, it makes sense to assume that the driver starts driving when he(/she) is in a condition allowing him to drive, meaning that he is vigilant and thus not too drowsy. Of course, the time when he first reaches the reference level of drowsiness would seem particularly important. If one wishes to know whether the driver is going to reach the reference level at some point in the future, one must make predictions.

A next important term is that of "reference band", which is defined by two reference levels. In the case of two reference levels, and thus of a reference band, one can define the notion of "time in reference band", which is the sum of all the continuous time intervals where the signal x(t) is in the reference band. While the present description is limited to two such reference levels, generalizations to more than two reference levels are easy to produce by the person skilled in the art.

Suitably the device further comprises a means to alert when the predicted state of the human being is in a particular relation with respect to one or more reference levels or reference bands. Such a means to alert may differ from one situation to another. For example, in a device that is suited to predict drowsiness of a driver of a car, each manufacturer will typically want to design its own alarm system in combination with the device according to the invention.

The predicted state of the human being as obtained by the device may be a prediction value (or scalar), or it may be a prediction signal (or function or sequence or vector) that starts at the present time. Below, preferred states of the human being will be described when the predicted state of the human being is a prediction value (System 1) and four descriptions when the predicted state of the human being is a prediction signal (Systems 2 to 5).

The application of the five systems to be described below to the input signal(s) can produce five distinct predictions (values or signals). One may lump any combination of the five systems into a single system that produces distinct predictions as described above.

Thus the device may suitably further comprise at least two means to predict at least two predicted state of the human being as specified in the descriptions of Systems 1 to 5 based on the same or different acquired data sets and means to generate a combined predicted state based on the at least two predicted states of the human being.

BRIEF DESCRIPTION OF THE DRAWINGS

The five systems will now be described in detail with reference to the accompanying figures listed and described below.

DETAILED DESCRIPTION OF THE INVENTION

System 1

In System 1, the predicted state of the human being is a value (or scalar) and preferably the predicted state of the human being is provided by one or more mathematical expressions or procedures describing the mathematical expectation of the time from the present moment at which the data as issued by the human being becomes greater than a specified reference level.

Figure 1:
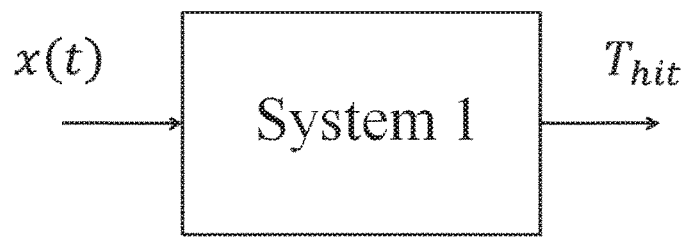
FIG. 1 shows a block diagram of System 1 with input and output.

In System 1, x(t) is the acquired data set or an input signal for $t \in [0, t_0]$, where $t_0$ is the present time/moment. System 1 takes x(t) and returns a scalar $T_{hit}$ that is the predicted time, on average, that x(t) passes through a certain reference level $y \in \mathbb{R}^+$ from the present time $t_0$, and that is called time of first hit. See FIG. 1. The only constraint for the input signal is that it be a realization (i.e. an instance) of a random process as described above.

System 1 includes three subsystems, namely sliding window, parameter estimator, and time predictor, and three control signals ($l_{window}$, $T_{sampling}$, y).

The sliding window takes a signal x(t) and returns a portion of this signal using a (unit) rectangular window. ("Unit" refers to the fact that the window preferably does not change the amplitude of the signal.) The length of the rectangular window could be controlled by a control signal ($l_{window}$). The length of the window is preferably optimized, in regard to the dynamics of x(t), the speed of the system, and the required accuracy for r(t). This window slides with the signal in time, typically so that the latest end of the window corresponds to the present time.

The parameter estimator takes the windowed signal and returns three fundamental parameters $\mu$, $\sigma$, Y(0) of a random process and preferably a GBM random process using the method described for System 3 below.

The time predictor uses the three fundamental parameters $\mu$, $\sigma$, Y(0) and returns $T_{hit}$, using the following formula, $$T_{hit} = E\{T\} = \frac{1}{v}\ln\left(\frac{y}{Y(0)}\right), \quad (1.1)$$

$$\text{where} = \mu - \frac{\sigma^2}{2},$$

Y(0) is the initial state, and y is the reference level and
T=inf{t≥0; X(t)≥y}, where inf gives the value of the smallest of the two arguments inside the brackets that follow it.

System 2

In System 2, the predicted state of the human being is provided by one or more mathematical expressions or procedures describing the probability that the value of the data as issued by the human being is between two specified reference levels for a time t in the future.

Figure 2:
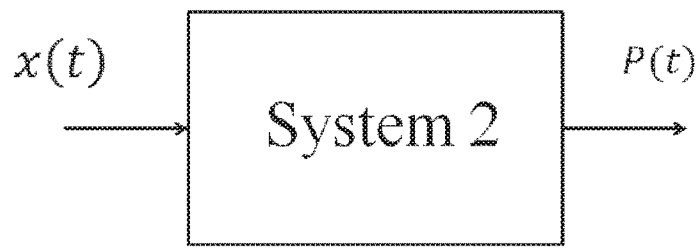
FIG. 2 shows a block diagram of System 2 with input and output.

In System 2, x(t) is the acquired data set or an input signal for $t \in [0, t_0]$, where $t_0$ is the present time/moment. System 2 takes x(t) and returns the function P:[0, ∞)→[0, 1], where P(t) denotes the probability that x(t) is limited by two reference levels $c_1 \in \mathbb{R}^+$ and $c_2 \in \mathbb{R}^+$ such that $c_1 < c_2$ at any given time t in the future. The interval $[c_1, c_2]$, usually called danger band or reference band. See FIG. 2. The only constraint for the input signal is that it be a realization (i.e. an instance) of a random process as described above.

System 2 includes three subsystems, namely sliding window, parameter estimator, and probability predictor and four control signals ($l_{window}$, $T_{sampling}$, $c_1$, $c_2$).

The sliding window takes a signal x(t) and returns a portion of this signal using a (unit) rectangular window. The length of the rectangular window may be controlled by a control signal ($l_{window}$). The length of the window is preferably optimized, in regard to the dynamics of x(t), the speed of the system, and the required accuracy for r(t). This window slides with the signal in time, typically so that the latest end of the window corresponds to the present time.

The parameter estimator takes the windowed signal and returns three fundamental parameters $\mu$, $\sigma$, Y(0) of a random process and preferably a GBM random process using the method described for System 3 below.

The probability predictor takes three fundamental parameters $\mu$, $\sigma$, $Y(0)$ and returns $P(t)$, using the following formula which is fully obtained in Hackman, S. T. (2006), Stock price dynamics and related topics, Georgia Institute of Technology:

$$P(t) = P(c_1 < X(t) < c_2) = \Phi\left(\frac{\ln \hat{c}_2 - vt}{\sigma\sqrt{t}}\right) - \Phi\left(\frac{\ln \hat{c}_1 - vt}{\sigma\sqrt{t}}\right), \quad (2.1)$$

where $= \mu - \frac{\sigma^2}{2}$, $Y(0)$ is the initial state, $\hat{c}_1 = \frac{c_1}{Y(0)}$, $\hat{c}_2 = \frac{c_2}{Y(0)}$, and $$\Phi(x) = \frac{1}{2}\left[1 + erf\left(\frac{x}{\sqrt{2}}\right)\right], \quad (2.2)$$

where $\Phi$ is the cumulative density function (CDF) of the unit-variance normal distribution $N(0, 1)$.

System 3

In System 3 the predicted state of the human being is provided by one or more mathematical expressions or procedures describing the risk that the data as issued by the human being reaches and becomes greater than a specified reference level for a time t in the future.

In System 3, $x(t)$ is the acquired data set or an input signal for $t \in [0, t_0]$, where $t_0$ is the present time/moment. System 3 takes $x(t)$ and returns a function $r: [0, +\infty) \to [0, +\infty)$, where r denotes the risk that $x(t)$ passes through a reference level $y \in \mathbb{R}^+$ at any given time t in the future. See FIG. 3. The only constraint for the input signal is that it be a realization (i.e. an instance) of a random process, preferably the aforementioned Geometric Brownian Motion (GBM) random process.

One of the main challenges when designing such a system as described above is to establish an appropriate and mathematically correct definition for the risk. The authors of a report of the Society for Risk Analysis (SRA) concluded after four years of research that it was impossible to establish a unique mathematically correct definition for the risk. Therefore, the risk should always be defined according to the domain of its application.

Applicant has found that, when the mathematical function describing the risk is based on a survival analysis, good results are obtained. Survival analysis is a body of knowledge that generally relates to the field of statistics and is for example described in David G. Kleinbaum. (2005), Survival Analysis (pp. 4-14), Springer. The main uses of survival analysis are in the study of cancer, oncology, the study of effectiveness of a medication, and health in general. To define the risk, it is required to present the four fundamental concepts of event, time to event, survivor function, and instantaneous potential.

By event is meant death, accident, exceeding a certain reference level, disease incidence, or any designated experience of interest that may happen. An event may also be referred to as a failure, because the event of interest usually is death, accident, or some other negative experience. The time until an event occurs is usually called "time to event" and usually shown by T. Usually the "time to event" quantity is referred to as survival time, because this parameter gives the time that an individual (or entity of interest) has "survived" over some follow-up period.

The survivor function $S(t)$ gives the probability that a person (or entity of interest) survives longer than some specified time t. It is defined as follows, $$S(t) = P(T > t), \quad (3.1)$$

where $P(.)$ denotes the "probability" (of an event), T the "time to event" random variable, and t some specific realization of this random variable. $S(t)$ is the probability that the random variable T exceeds the specified time t. $S(t)$ is a usual function of t. Theoretically, as t ranges continuously from 0 up to infinity, the survivor function can be graphed as a smooth curve. Note that one only considers the non-negative values of t.

All survivor functions have the following characteristics:
1) They are non-increasing; that is, they head downward as t increases.
2) At time $t=0$, $S(t)=S(0)=1$; that is, at the start of the study, since no one has gotten the event yet, the probability of surviving past time 0 is 1.
3) At time $t=\infty$, $S(t)=S(\infty)=0$; that is, theoretically, if the study period increased without limit, eventually nobody would survive, so the survivor curve must eventually fall to zero.

To get an idea of what is meant by instantaneous potential, an illustration is now given in the case of the speed of a car. If, for example, a person is driving in a car and he(/she) sees that his speedometer is registering 60 miles per hour (mph), what does this reading mean? It means that if, in the next hour, he continues to drive in this way, with the speedometer exactly on 60, he would cover 60 miles. This reading gives the potential, at the moment he looks at his speedometer, of the number of miles he may travel in the next hour. However, because he may slow down or speed up or even stop during the next hour, the 60-mph speedometer reading does not tell him the number of miles that he will really cover in the next hour. The speedometer only tells him how fast he is going at a given moment; that is, the instrument provides the instantaneous potential or velocity.

Using above concepts, the risk is defined as an instantaneous potential per unit time for the event to occur, given that the individual (or entity of interest) has survived up to time t. It is possible to obtain the risk at any given time t using the risk function, also referred to as the hazard function, $r(t)$, which is expressed as follows, $$r(t) = \lim_{\Delta t \to 0} \frac{P(t \leq T < t + \Delta t \mid T \geq t)}{\Delta t}, \quad (3.2)$$

where T is time to event random variable, $P(t \leq T \leq t+\Delta t | T \geq t)$ gives the probability that a person's survival time T will lie in the time interval between t and $t+\Delta t$, given that the survival time T is greater than or equal to t.

When one takes the limit of the expression (fraction) on the right-hand-side as the time interval approaches zero, one obtains an expression for the instantaneous probability of failing at time t per unit time. Another way of saying this is that the risk function $r(t)$ gives the instantaneous potential for failing at time t per unit time, given survival up to time t. The risk function $r(t)$ has the following characteristics:
1) It is always nonnegative, that is, equal to or greater than zero.
2) It has no upper bound.

The two functions $S(t)$ or $r(t)$ are mathematically related by the following formulas as described in David G. Kleinbaum (2005), Survival analysis, p. 14, Springer:

$$S(t) = \exp\left(-\int_0^t h(u)du\right), \quad (3.3)$$

$$r(t) = -\left(\frac{dS(t)/dt}{S(t)}\right), \quad (3.4)$$

where $dS(t)/dt$ the time derivative of the survivor function $S(t)$

This means that, given one of them, one can get the other. In other words, one can work with either of them.

Figure 4:
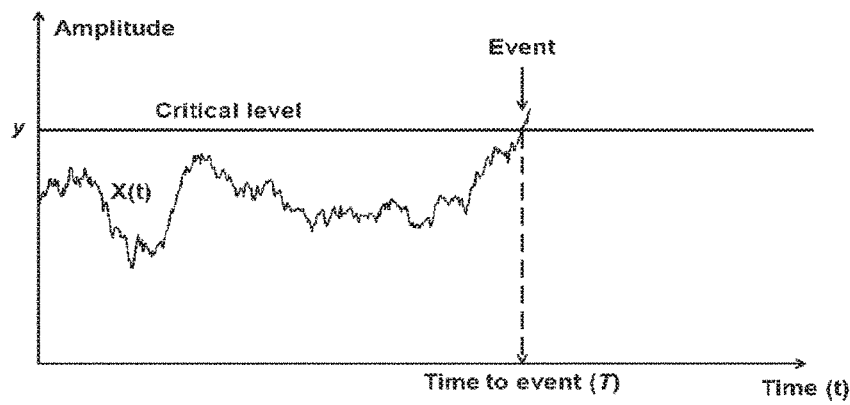
FIG. 4 shows an illustration of the concept of "time of first hit".

To establish the equations describing the operation of System 3, a survival analysis is performed as will be described below. Let's define as event the first passage of the GBM random process $X(t)$ through a reference level $y \in \mathbb{R}^+$. This is illustrated in FIG. 4.

In the present method, the risk function $r(t)$ for $t \in [t_0, +\infty)$ where $t_0$ is the present time is found, wherein it is assumed that the fundamental parameters of $X(t)$ are known.

Conventional methods of survival analysis to obtain the risk function are only able to deal with either constant or time-variable function covariates. In other words, the conventional methods of survival analysis have been designed to work in deterministic environments. In the present method, $X(t)$ is however a random process. In general, survival in a dynamic environment is a difficult and mathematically sophisticated subject. In the method of this invention, the sophisticated mathematical concepts have been simplified. Before describing our method to find the risk function, two particular types of random processes are introduced, i.e. the Brownian Motion random process and the Geometric Brownian Motion random process.

To introduce the Brownian Motion (BM) random process, one typically starts by introducing the Standard Brownian Motion (SBM) random process.

Standard Brownian Motion (SBM) is a random process $\{B(t): t \geq 0\}$ with the following properties:
I. It always starts at 0, i.e., $B(0)=0$.
II. It possesses stationary and independent increments.
III. Each sample path (i.e. realization) $B(\omega, .)$ is continuous (almost surely).
IV. $B(t+S)-B(t) \sim N(0, S)$.

Above, $N(\mu, \sigma)$ denotes a normal (or Gaussian) distribution (or more precisely probability density function) with mean $\mu$ and standard deviation $\sigma$.

A random process $\{X(t): t \geq 0\}$ is called Brownian Motion (BM) with parameters $(\mu, \sigma)$ if it may be represented as $$X(t)=X(0)+\mu t+\sigma B(t), \quad (3.5)$$

where $B(t)$ is Standard Brownian Motion and $X(0)$ is independent of $B(t)$. $X(0)$ is a random variable and $B(t)$ is a random process. By using property IV above, one can obtain the relation $$X(t+s)-X(t)=\mu s+\sigma B(s) \sim N(\mu s, \sigma^2 s). \quad (3.6)$$

The parameter $\mu$ is called the drift of the random process $X$, and the parameter $\sigma^2$ is called the variance of the random process $X$. The symbol $B$ will be reserved for Standard Brownian Motion, for which $\mu=0$ and $\sigma^2=1$.

A random process $\{Y(t): t \geq 0\}$ is said to be a geometric Brownian motion random process if it may be represented in the form $$Y(t)=Y(0)e^{X(t)}, \quad (3.7)$$

where $X$ is a $(v, \sigma)$ Brownian motion random process, where $v$ is related to $\mu$ and $\sigma$ via $v=\mu-\sigma^2/2$, and $Y(0)$ is a positive constant independent of $X$. Note that each sample path (i.e. realization) of the $Y$ random process is strictly positive. By taking the natural logarithm of both sides of (3.7), the following formula is obtained:

$$\ln \frac{Y(t)}{Y(0)} \sim N(vt, \sigma^2 t). \quad (3.8)$$

A random variable whose natural logarithm has a normal distribution is called a lognormal random variable and its distribution is called a lognormal distribution. It is possible to easily simulate a GBM random process for discrete instants $t_0 < t_1 < \ldots < t_n$ using the following recursive formula, $$Y(t_{i+1}) = Y(t_i)\exp\left(\left[\mu - \frac{\sigma^2}{2}\right](t_{i+1} - t_i) + \sigma\sqrt{t_{i+1} - t_i}\, Z_{i+1}\right), \quad (3.9)$$

where $Z_1, Z_2, \ldots, Z_n$ are independent random variables drawn from the standard normal distribution.

As an example, the above formula (3.9) is used to generate ten different realizations of a GBM random process with the following characteristics:

$\sigma=0.5$, $\mu=0.5$, $\Delta t=t_{i+1}-t_i=0.0032$, steps=250, $Y(0)=100$.

Figure 5:
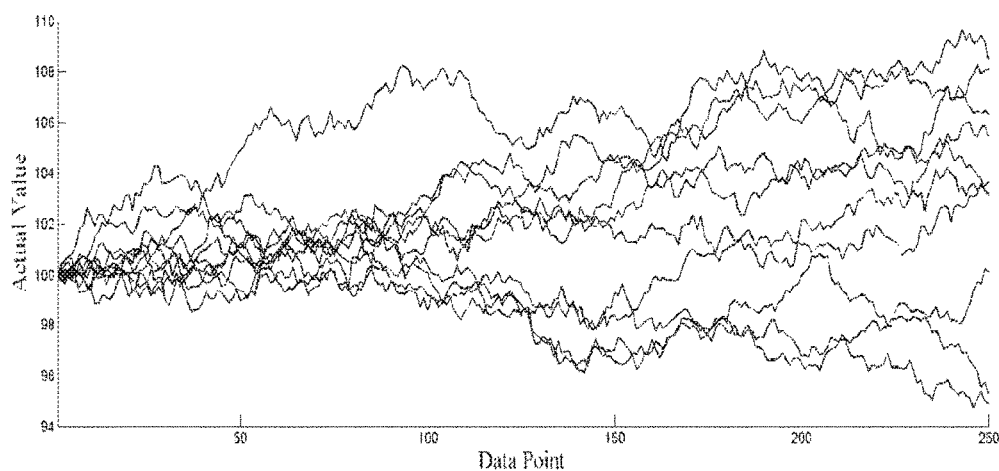
FIG. 5 shows ten different realizations of a geometric Brownian motion (GBM) random process with the following parameters: $\sigma=0.5$, $\mu=0.5$, $\Delta t=t_{i+1}-t_i=0.0032$, steps=250, Y(0)=100.

The results are shown in FIG. 5.

The variable $Y_k$, $0 \leq k < \infty$, follows a GBM random process (with drift parameter $\mu$ and volatility parameter $\sigma$) if, for all nonnegative values of k and t, the (ratio) random variable $$\frac{Y_{k+t}}{Y_k}$$

is independent of all similar (ratio) random variables for all values of the index k up to the present and if, in addition, $$\ln\left(\frac{Y_{k+t}}{Y_k}\right)$$

has a normal distribution with mean $\mu t$ and variance $\sigma^2 t$, independent of k, where $\mu$ and $\sigma$ are constant.

Therefore $Y_k$, $0 \leq k < \infty$, follows a GBM random process if two following constraint satisfied:
I. Normality for the log ratios ($W_i=\ln(Y_{i+1})-\ln(Y_i)$) with the constant mean and variance.
II. Independence from previous data (log ratios independent of their past values).

The simplest, but not very accurate, way to check for normality is to plot a histogram of the log ratios and to compare it visually to a normal distribution plot.

Another graphical method for testing the normality assumption is to examine the normal probability plot. A normal probability plot, also known as a normal quantile-quantile plot or Q-Q plot, is the plot of the ordered data values against the associated quantiles of the normal distribution. For data from a normal distribution, the points of the plot should lie close to a straight line.

The statistical tests of normality can be conducted in many ways by using any of the goodness-of-fit tests on the $W_i$ values. One way is to run a chi-square test for goodness-of-fit. Another goodness-of-fit test is the Shapiro-Wilk W Test. In this test, the hypothesis set is:

$H_0$: The distribution is normal, against
$H_1$: The distribution is not normal.

The test gives the value of the statistic W and the corresponding p-value. The p-value is compared to the specified level of significance $\alpha$. If the observed p-value is greater than the level of significance, the test statistic is not in the rejection region, and the null hypothesis of a normal distribution cannot be rejected. Note that a large p-value does not definitively identify the data as normally distributed; it only means that the data could plausibly have been generated by a normal distribution.

Figure 10:
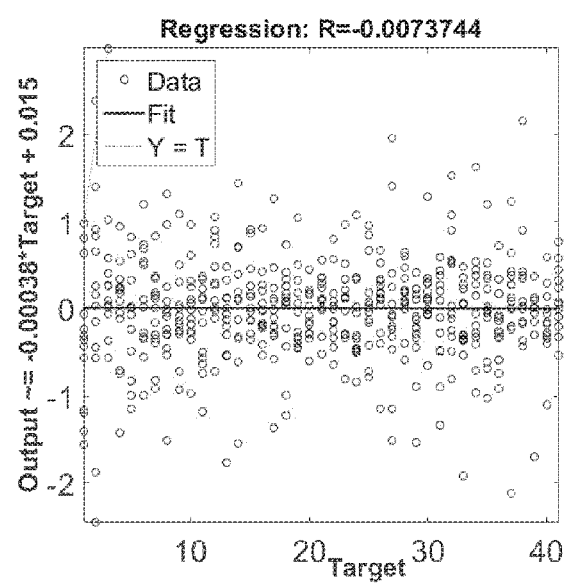
FIG. 10 shows a regression plot of the log ratios and time for the level of drowsiness (LoD) for Case A (corresponding to first morning, with low LoD).

One of the easiest methods to check the independency of log ratios is to plot the $W_i$'s with respect to i. The lack of any visible pattern indicates independency for successive log ratios. FIG. 10 of the illustrating example is an example of such a plot.

A GBM random process is suitably characterized by two fundamental parameters, i.e. $v=\mu-\sigma^2/2$ and $\sigma$. These parameters may be estimated accurately from a single or multiple realizations of a GBM random process according to the following procedure:

Let $X_i = \ln(Y_i) - \ln(Y_{i-1})$ and $$\hat{m} = \sum_{i=1}^{n} \frac{x_i}{n}, \quad (3.10)$$

$$\hat{v} = \sum_{i=1}^{n} \frac{(x_i - \hat{m})^2}{n}, \quad (3.11)$$

where n is the total number of log ratios. Then it is possible to estimate $\hat{\mu}$ and $\hat{\sigma}$ using the following equations, $$\hat{m} = \left[\hat{\mu} - \frac{1}{2}\hat{\sigma}^2\right]\Delta t, \quad (3.12)$$

$$\hat{v} = \hat{\sigma}^2 \Delta t, \quad (3.13)$$

where $\Delta t$ is the time step $\Delta t = t_{i+1} - t_i$, where the $t_i$'s appear above.

The risk function for a GBM random process is subsequently computed using the thus obtained Brownian motion (BM) random process and Geometric Brownian Motion (GBM) random process and their properties. The determination of the risk function for a GBM random process is based on performing the following steps:

Step 1: find the survivor function for a GBM random process with initial state X(0)=0.

Step 2: perform a change of variable in the survivor function obtained in "Step 1" to obtain a survivor function for a GBM random process with initial state $Y(0)=Y_1$, wherein Y(0) is the initial state and $Y\_1 \in \mathbb{R}^+$.

Step 3: convert the survival function to the risk function using relation (3.4).

By applying this innovative procedure, the risk function formula for the GBM random process is obtained. As a check, one can verify that the obtained risk function obeys all required properties of risk functions as described above.

Applicants believe that the above approach is new and inventive. The approach is described in more detail below:

Step 1. Let X(t) represent a BM random process such that X(0)=0. For each t, let $M_t$ denote the maximum value of X on the interval [0, t]. For any $y \in \mathbb{R}^+$, the following can be written:

$$P(M_t < y) = \Phi\left(\frac{y - \mu t}{\sigma\sqrt{t}}\right) - e^{2\mu y/\sigma^2} \Phi\left(\frac{-y - \mu t}{\sigma\sqrt{t}}\right), \quad (3.14)$$

where $$\Phi(x) = \frac{1}{2}\left[1 + \text{erf}\left(\frac{x}{\sqrt{2}}\right)\right], \quad (3.15)$$

where is $\Phi$ is the cumulative density function (CDF) of the unit normal distribution N(0, 1). For $y \in \mathbb{R}^+$, let T(y) denote the first time t at which $X_t = y$. It is called the one-sided hitting time or, synonymously, the one-sided passage time. Now this quantity is the earlier referred to "time to event". It should be clear that $$P(T(y) > t) = P(M_t < y). \quad (3.16)$$

From (3.1), (3.10), and (3.16), the following formula follows:

$$S(t) = \Phi\left(\frac{y - \mu t}{\sigma\sqrt{t}}\right) - e^{2\mu y/\sigma^2} \Phi\left(\frac{-y - \mu t}{\sigma\sqrt{t}}\right), \quad (3.17)$$

where S(t) is the survivor function for a ($\mu$, $\sigma$) Brownian Motion (BM) random process.

Step 2. According to (3.7), $$\ln\left(\frac{Y(t)}{Y(0)}\right)$$

is a (v, $\sigma$) BM random process, where $v = \mu - \sigma^2/2$. So it is possible to obtain survivor function for a GBM random process only by substituting v into $\mu$ and $$\ln\left(\frac{y}{Y(0)}\right)$$

into y in (3.17) resulting in:

$$S(t) = \Phi\left(\frac{\ln\left(\frac{y}{Y(0)}\right) - vt}{\sigma\sqrt{t}}\right) - e^{2vln(y/Y(0))/\sigma^2} \Phi\left(\frac{-\ln\left(\frac{y}{Y(0)}\right) - vt}{\sigma\sqrt{t}}\right), \quad (3.18)$$

where S(t) is the survivor function for a GBM random process.

Step 3. S(t) is converted to r(t). From (3.4) and (3.18), the risk function r(t) for the GBM random process can be expressed as follows:

$$r(t) = \frac{\frac{\sqrt{2}\beta_3}{\beta_5} + \beta_2}{\sqrt{\pi}\exp\left(\frac{\beta_3^2}{\beta_6}\right)} + \frac{\beta_1\left(\frac{\sqrt{2}\beta_4}{\beta_5} - \beta_2\right)}{\sqrt{\pi}\exp\left(\frac{\beta_4^2}{\beta_6}\right)}}{\frac{\text{erf}\left(\frac{\sqrt{2}\beta_3}{2\sigma\sqrt{t}}\right)}{2} + \beta_1\left(\frac{\text{erf}\left(\frac{\sqrt{2}\beta_4}{2\sigma\sqrt{t}}\right)}{2} - \frac{1}{2}\right) + \frac{1}{2}}, \quad (3.19)$$

-continued where $$\beta_1 = \exp\left(\frac{2\nu\ln\left(\frac{y}{Y(0)}\right)}{\sigma^2}\right),$$

$$\beta_2 = \frac{\sqrt{2}\,\nu}{2\sigma\sqrt{t}},$$

$$\beta_3 = \ln\left(\frac{y}{Y(0)}\right) - \nu t,$$

$$\beta_4 = \ln\left(\frac{y}{Y(0)}\right) + \nu t,$$

$$\beta_5 = 4\sigma\sqrt{t^3},$$

$$\beta_6 = 2\sigma^2 t,$$

where y is the reference level and Y(0) is the initial value.

Figure 3:
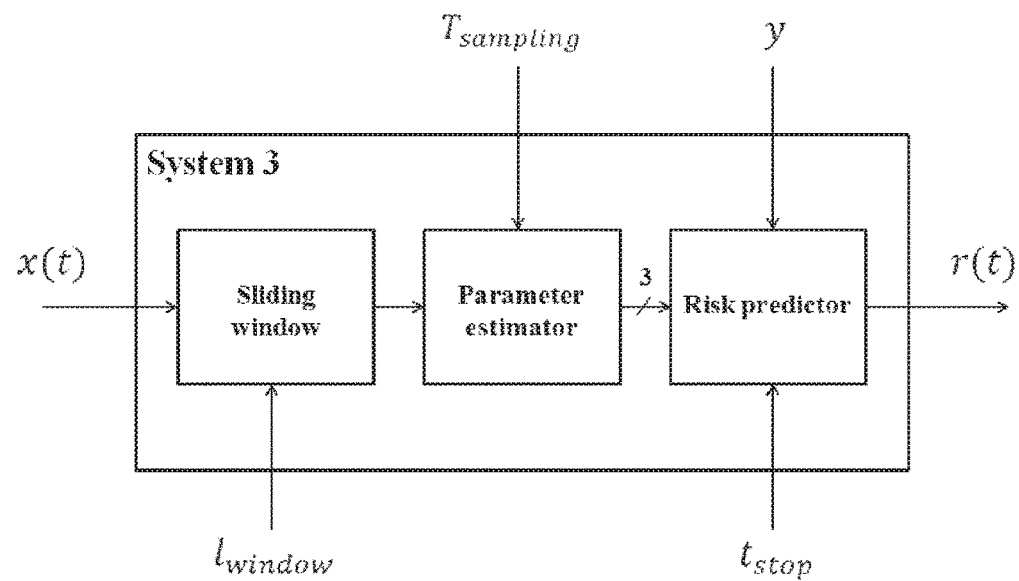
FIG. 3 shows a block diagram of System 3 with input and output.

System 3 further includes three subsystems, namely sliding window, parameter estimator, and risk predictor and four control signals ($l_{window}$, $t_{stop}$, y, $T_{sampling}$) as shown in FIG. 3.

The sliding window takes a signal x(t) and returns a portion of this signal as the acquired data set using a (unit) rectangular window. The length of the rectangular window could be controlled by a control signal ($l_{window}$). The length of the window is preferably optimized, in regard to the dynamics of x(t), the speed of the system, and the required accuracy for r(t). This window slides with the signal in time, typically so that the latest end of the window corresponds to the present time.

The parameter estimator takes the windowed signal and sampling period ($T_{sampling}$) and returns three fundamental parameters μ, σ, Y(0) of a GBM random process using the method described above.

The risk predictor takes the three fundamental parameters μ, σ, Y(0), as well as the reference level y∈ℝ$^+$, and returns the risk function r(t) using formula (3.19). The range of the risk function is [0, +∞) but usually it is computed for a limited period of time[0, $t_{stop}$). The prediction system thus returns a signal that consists in all the values of the risk function over the range from the present time up to the maximum value of time desired.

System 4

In System 4, the predicted state of the human being is provided by one or more mathematical expressions or procedures describing the probability that the data issued by the human being reaches and becomes greater than a specified reference level for a time t in the future.

Figure 6:
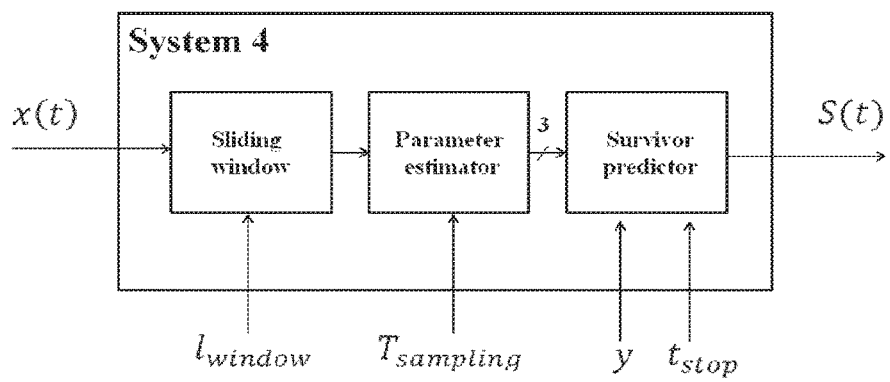
FIG. 6 shows a block diagram of System 4 with input and output.

System 4 is similar to System 3 except in that System 4 takes a realization of a GBM random process as input signal and returns the survival function instead of the risk function as illustrated in FIG. 6.

System 5

In System 5 the predicted state of the human being is provided by one or more mathematical expressions or procedures describing the probability that the data as issued by the human being remains lower than a specified reference level at all times greater than t for a time t in the future.

Figure 7:
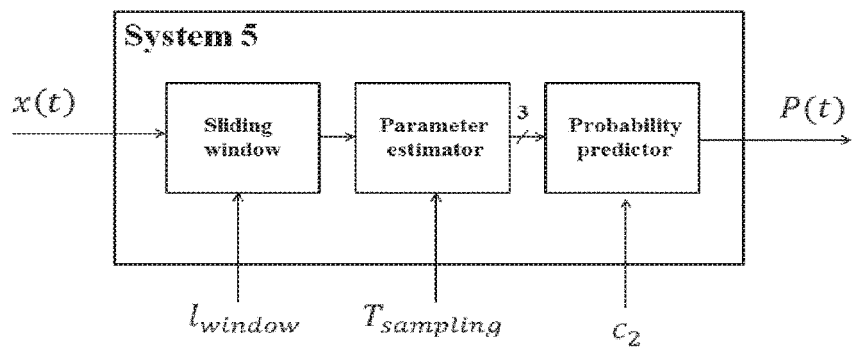
FIG. 7 shows a block diagram of System 5 with input and output.

System 5 is quite similar to System 2. The only difference is that, in System 5, the control signal $c_1$ is set to zero as illustrated in FIG. 7. Another way of saying this is that the lower bound is always zero. Therefore, it returns the probability that the signal does not pass through the reference level $c_2$ at any given time in the future.

The above prediction device according to the invention may find application for many different data sets issued by a human being, as, for example, applicant has found that it is especially useful when the predicted state of the human being relates to drowsiness, somnolence, fatigue, reduced vigilance, and/or cognitive distraction. Examples of useful data as issued by the human being relating to drowsiness are the level of drowsiness (LoD), average of reaction time, average of eyelid closure speed, average of eyelid opening speed, average of closed eyes duration, and percentage of eye closure. In a device or application of the invention, all or a selection of these signals may be used. Most preferably, the predicted state of the human being relates to drowsiness and the data signal as issued by the human being comprises the level of drowsiness (LoD) and the means to acquire the data is based on polysomnography (PSG) or photooculography (POG) or other imaging Such a device may find use in combination with a means of transportation, and more preferably when the prediction device is used to prevent drowsy driving.

The invention is also directed to a method for a real time prediction for drowsiness wherein a human being issues a level of drowsiness or one or more ocular parameters indicative for drowsiness as data and wherein the method comprises the following steps, (a) the data is acquired from inside or outside the human being for one or more time periods located in a time interval comprised from a moment in the past to the present moment to obtain an acquired data set, (b) the acquired data set is modelled as a geometric Brownian motion (GBM) random process model or an Ito process (IP) random process model to obtain a fitted random process model, and (c) wherein a real time prediction of a state of drowsiness of the human being is obtained using the fitted random process model.

The preferred embodiments and illustrative uses of this method are the measures and examples described above for the device according to the invention and especially the following. In step (b), the acquired data set is suitably modelled as a geometric Brownian motion (GBM).

The method suitably comprises a step (d) wherein an alert is activated when the predicted state of drowsiness relates to one or more reference levels or reference bands.

The level of drowsiness or an ocular parameter indicative for drowsiness data as issued by the human being is suitably one or more of the following data: level of drowsiness (LoD), average of reaction time, average of eyelid closure speed, average of eyelid opening speed, average of closed eyes duration and/or percentage of eye closure. The level of drowsiness (LoD) is suitably acquired in step (a) via polysomnography (PSG) or via photooculography (POG) or via other imaging.

The predicted state of the human being is suitably provided by one or more mathematical expressions or procedures describing the risk that the data as issued by the human being reaches and becomes greater than a specified reference level for a time t in the future, wherein the mathematical expressions or procedures describing the risk are based on a survival analysis, wherein the device comprises means to obtain the mathematical function describing the risk function for a geometric Brownian (GBM) random process model by performing the following steps:

Step 1: find the survivor function for a GBM random process model with initial state X(0)=0.

Step 2: perform a change of variable in the survivor function obtained in "Step 1" to obtain a survivor function for a GBM random process model with initial state Y(0)=Y_1.

Step 3: convert the survival function to the risk function using relation:

$$r(t) = -\left(\frac{dS(t)/dt}{S(t)}\right),$$

wherein t is time, r(t) is the risk function, X(t) is the data issued by the human being, and S(t) is a survivor function.

The invention is further directed to a computer program configured to model an acquired data set as a random process model to obtain a fitted geometric Brownian motion (GBM) random process model or an Ito process (IP) random process model, and predicting the state of a human being using the fitted random process model to obtain a predicted state of the human being, wherein the acquired data set is obtained from inside or outside the human being for one or more time periods in the past, up to the present.

Preferably such a computer program is used as part of a device according to the invention.

Preferably the random process model is based on a geometric Brownian motion (GBM) random process model, as described for the device.

The acquired data set comprises of one or more of each of a signal, temporal signal, spatial signal, or spatial-temporal signal, as described for the device.

The program further comprises a means to alert when the predicted state of the human being reaches one or more reference levels or is between reference bands, as described for the device.

The predicted state of the human being is provided by one or more mathematical expressions or procedures describing the mathematical expectation of the time from the present moment at which the data as issued by the human being becomes greater than a specified reference level, as described for the device.

The predicted state of the human being is provided by one or more mathematical expressions or procedures describing the probability that the value of the data as issued by the human being is between two specified reference levels for a time t in the future, as described for the device.

The predicted state of the human being is provided by one or more mathematical expressions or procedures describing the risk that the data as issued by the human being reaches and becomes greater than a specified reference level for a time t in the future, as described for the device.

The mathematical expressions or procedures describing the risk are based on a survival analysis, wherein the device comprises means to obtain the mathematical function describing the risk function for a GBM random process model by performing the following steps:

Step 1: find the survivor function for a GBM random process model with initial state X(0)=0.

Step 2: perform a change of variable in the survivor function obtained in "Step 1" to obtain a survivor function for a GBM random process model with initial state Y(0)=Y_1.

Step 3: convert the survival function to the risk function using relation:

$$r(t) = -\left(\frac{dS(t)/dt}{S(t)}\right),$$

wherein t is time, r(t) is the risk function, X(t) is the data issued by the human being, and S(t) is a survivor function, and dS(t)/dt the time derivative of the survivor function S(t), as described for the device.

The predicted state of the human being is provided by one or more mathematical expressions or procedures describing the probability that the data as issued by the human being reaches and becomes greater than a specified reference level for a time t in the future, as described for the device.

The predicted state of the human being is provided by one or more mathematical expressions or procedures describing the probability that the data as issued by the human being remains lower than a specified reference level at all times greater than t for a time t in the future, as described for the device.

The computer program further comprises at least two means to predict at least two predicted states of the human being as described above based on the same or different acquired data sets and means to generate a combined predicted state of the human being based on the at least two predicted states of the human being.

The predicted state of the human being in said computer program may relate to drowsiness, somnolence, fatigue, reduced vigilance, and/or cognitive distraction.

Preferably the computer program is used in combination with a means of transportation, and more preferably to prevent drowsy driving.

The invention shall be illustrated by the following non-limiting example.

EXAMPLE

The example relates to the detection and prediction of drowsy driving. In this example, six different biological signals, i.e. level of drowsiness (LoD), average of reaction time, average of eyelid closure speed, average of eyelid opening speed, average of closed eyes duration, and percentage of eye closure, all related to drowsiness (and thus to vigilance too) were measured for 13 different subjects, under different test conditions (low, average, and high levels of drowsiness, or, more specifically, of sleep deprivation).

By applying the normality and independency tests as described above on the obtained results, it was shown that all these experimentally-obtained signals are realizations (or paths) of a GBM random process, regardless of the levels of sleep deprivation, and thus of drowsiness. It is the finding that these signals are realizations of GBM random processes that allows predicting the state of the human being and in particular the state of the human being related to the level of drowsiness (LoD).

Figure 8:
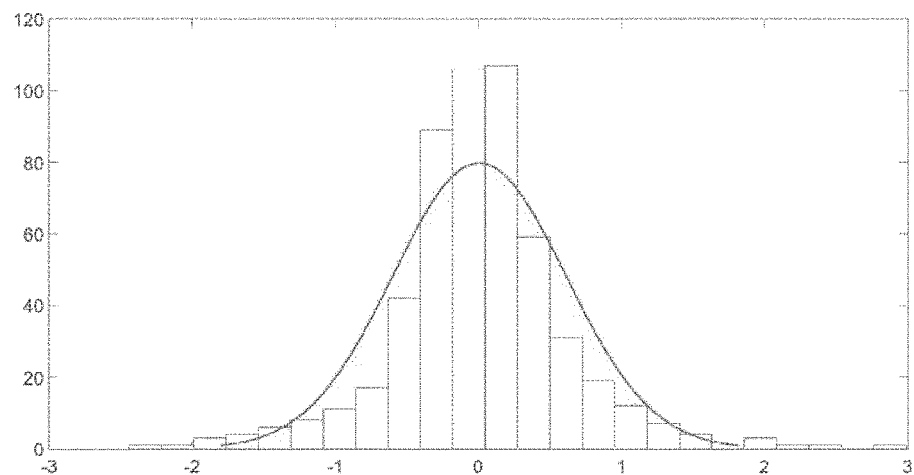
FIG. 8 shows a histogram of the log ratios for the level of drowsiness (LoD) for Case A (corresponding to first morning, with low LoD).
Figure 9:
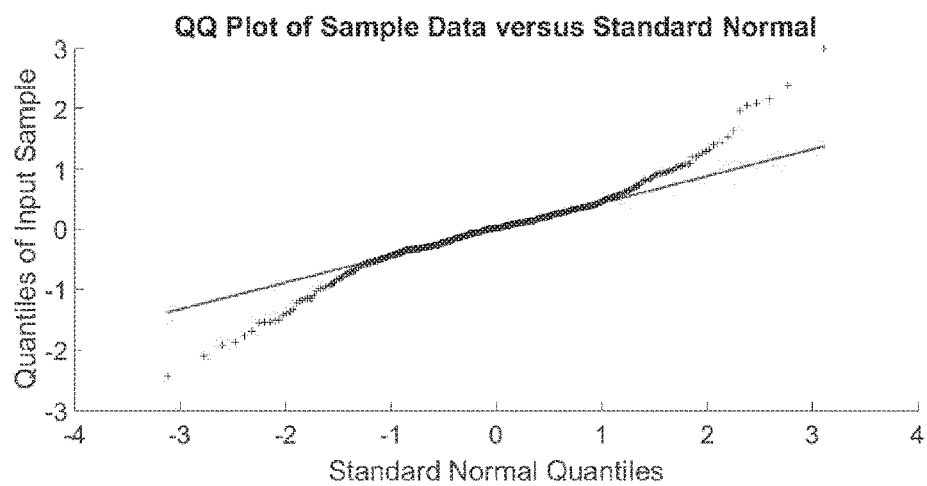
FIG. 9 shows a Q-Q plot of the log ratios for the level of drowsiness (LoD) for Case A (corresponding to first morning, with low LoD).

Reference is made to FIGS. 8 to 10, which show that the normality and independency constraints are satisfied, wherein FIG. 8 is a histogram of log ratios, FIG. 9 a log-ratios Q-Q plot, and FIG. 10 a log ratios with respect to time plot. Even though the Q-Q plot is slightly different from the ideal, the normality assumption is satisfied.

Figure 11:
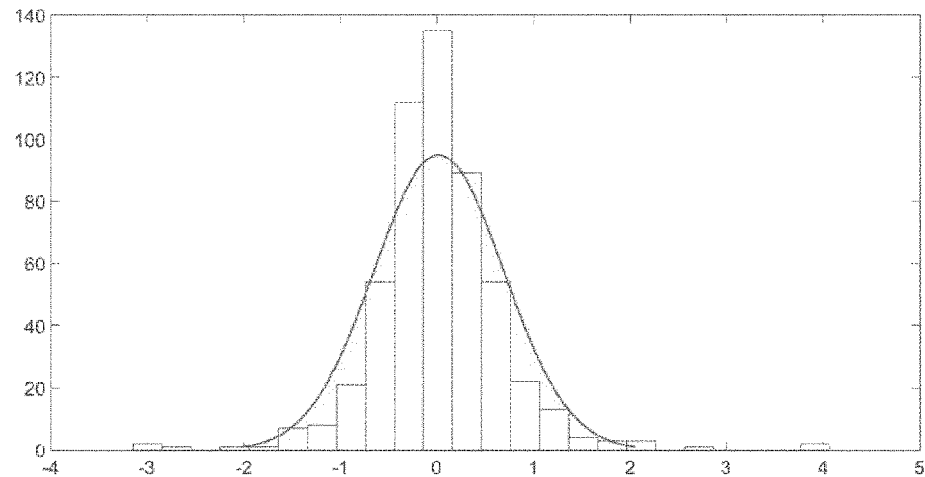
FIG. 11 shows a histogram of the log ratios for the level of drowsiness (LoD) for Case B (corresponding to afternoon, with average LoD).
Figure 12:
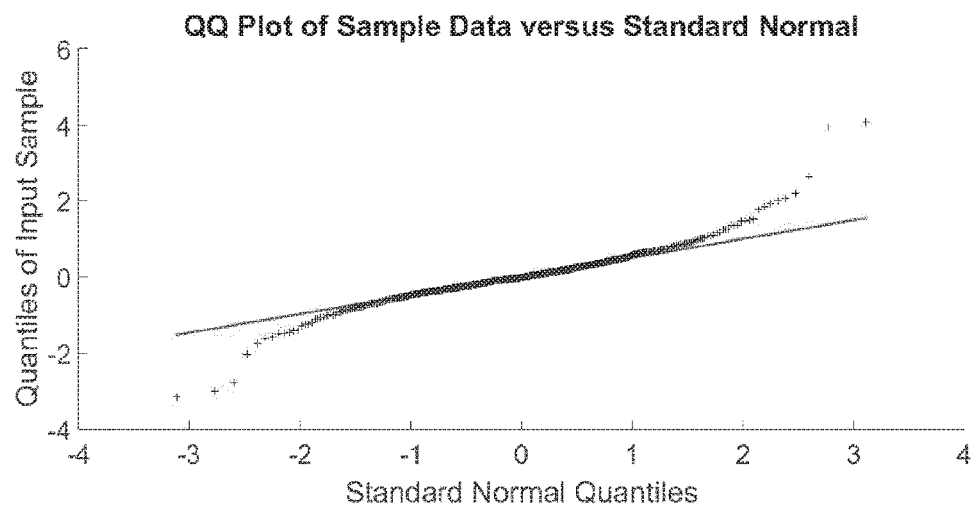
FIG. 12 shows a Q-Q plot of the log ratios for the level of drowsiness (LoD) for Case B (corresponding to afternoon, with average LoD).
Figure 13:
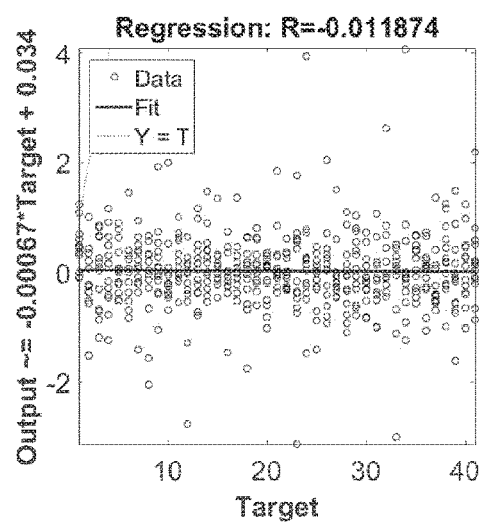
FIG. 13 shows a regression plot of the log ratios and time for the level of drowsiness (LoD) for Case B (corresponding to afternoon, with average LoD).

Reference is made to FIGS. 11 to 13, which show that the normality and independency constraints are perfectly satisfied.

Figure 14:
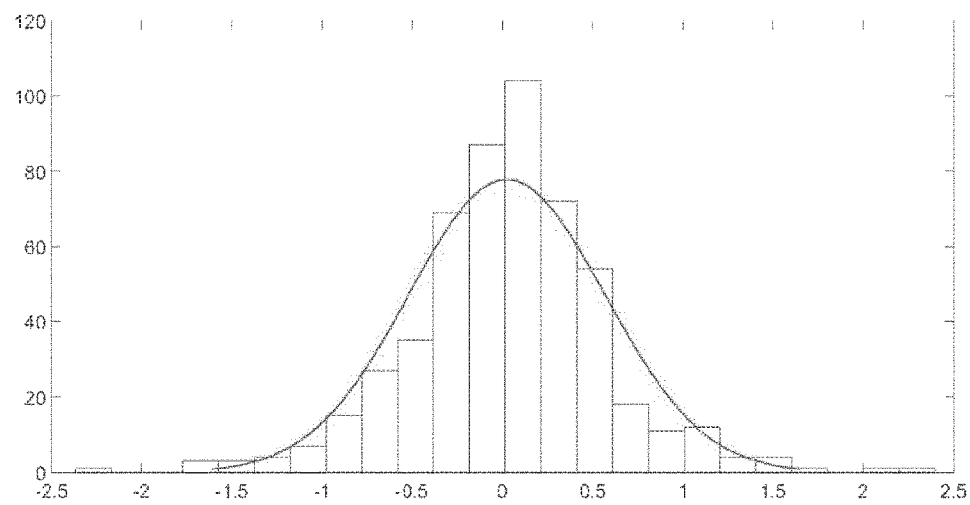
FIG. 14 shows a histogram of the log ratios for the level of drowsiness (LoD) for Case C (corresponding to next morning, with high level of LoD).
Figure 15:
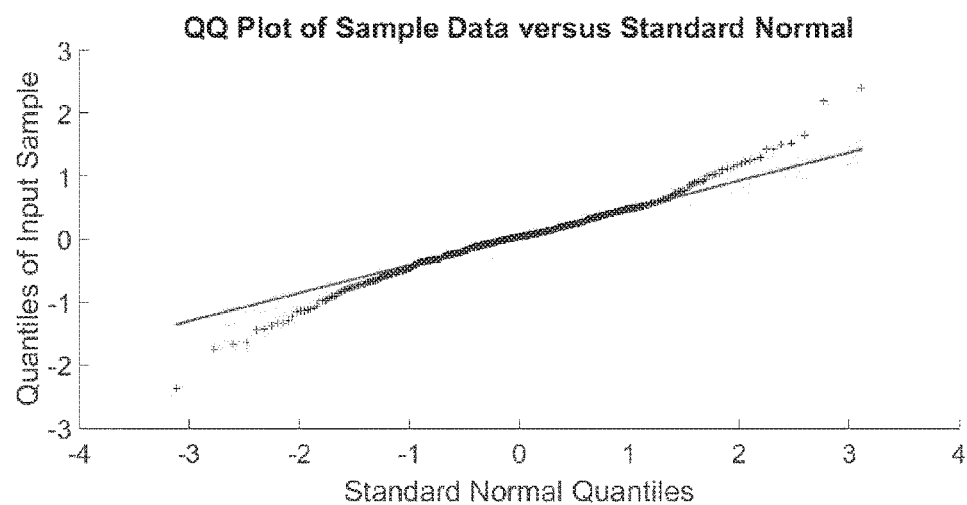
FIG. 15 shows a Q-Q plot of the log ratios for the level of drowsiness (LoD) for Case C (corresponding to next morning, with high level of LoD).
Figure 16:
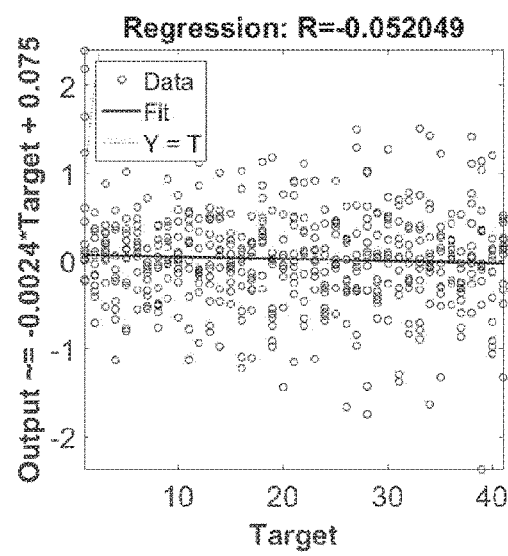
FIG. 16 shows a regression plot of the log ratios and time for the level of drowsiness for Case C (corresponding to next morning, with high level of LoD).

Reference is made to FIGS. 14 to 16, which show that the normality and independency constraints are perfectly satisfied.

Figure 17:
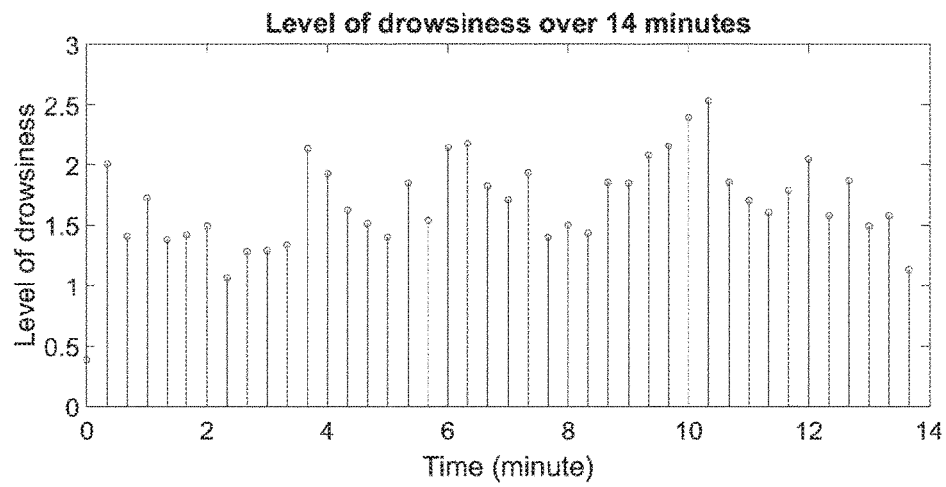
FIG. 17 shows an example of real, experimental input signal in Case A (corresponding to first morning, with low LoD).

Investigated was a Case A for low LoD as illustrated in FIG. 17, wherein signal Y(t) represents the level of drowsiness of a driver (where t=1 represents one minute and $$T_{sampling} = \frac{1}{3}\bigg).$$

The object was to compute the risk that the level of drowsiness passes through 9 for the next 5 minutes.

As the GBM assumption has already been verified for the level of drowsiness, it was possible to use System 3 to compute the risk for the next 5 minutes. Thus $$t_{stop} = 5, T_{sampling} = \frac{1}{3},$$

y=9, $1_{window}$=42 (meaning that the whole signal is used). The key functions are shown in FIGS. 18 and 19.

Figure 18:
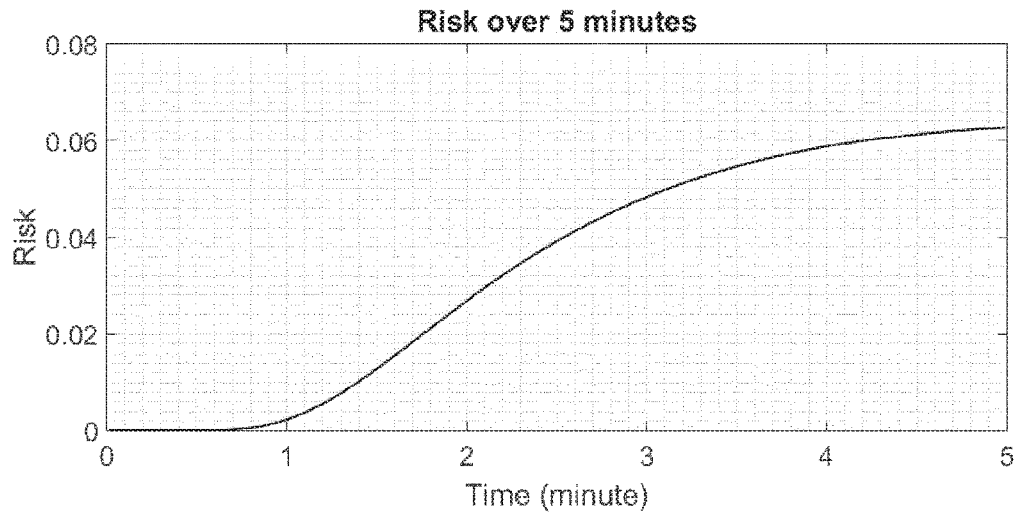
FIG. 18 shows an output from prediction device according to System 3 in Case A (corresponding to first morning, with low LoD) for input shown in FIG. 17.

FIG. 18 represents the risk function (or signal) for the next 5 minutes. The function shown exhibits all the necessary characteristics for a risk function. As one can see, the risk that the level of drowsiness passes through 9 is nearly zero for the next one minute, then it increases slightly with time; however, the values in the present case A, even at the peak, are still much smaller than in the next case B as will be discussed below.

Figure 19:
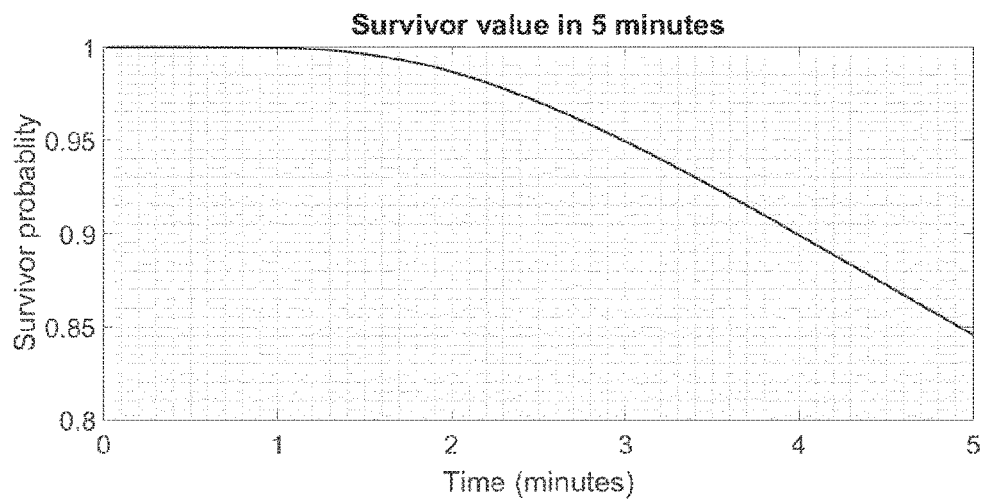
FIG. 19 shows an output from prediction device according to System 4 in Case A (corresponding to first morning, with low LoD) for input shown in FIG. 17.

FIG. 19 represents the survivor function (or signal) for the next five minutes. The function shown exhibits all the necessary characteristics for a survivor function. As one can see, the probability that the level of drowsiness doesn't pass through 9 is close to one for the next one and one-half minutes; then it decreases to 0.84 after at the end of the 5 minutes.

Figure 20:
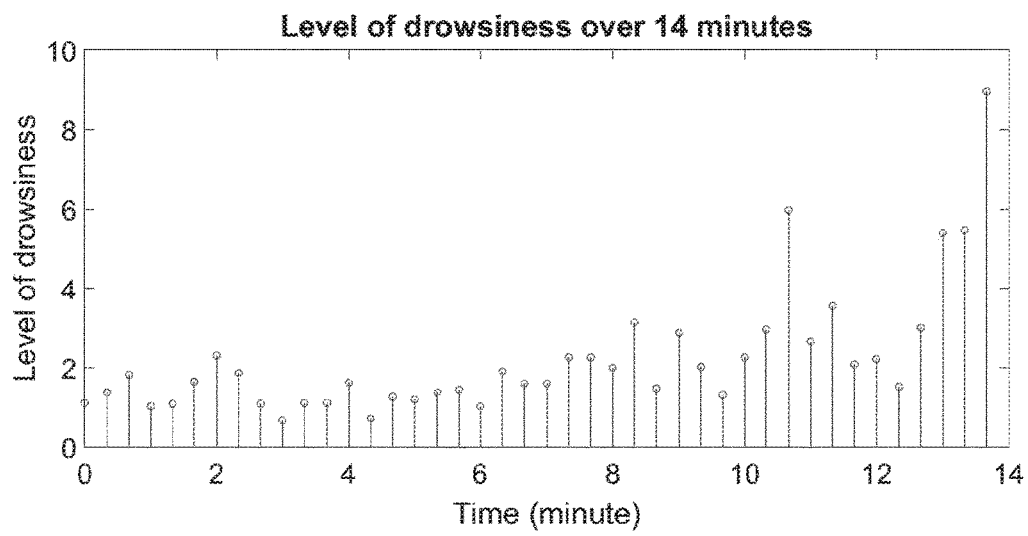
FIG. 20 shows an example of real, experimental input signal in Case B (corresponding to afternoon, with average LoD).

In a next Case B, the LoD was high as illustrated in FIG. 20, wherein signal Y(t) represents the level of drowsiness of a driver (t=1, represents 1 minute and $$T_{sampling} = \frac{1}{3}\bigg).$$

Again, the object was to compute risk that the level of drowsiness passes through 9 for the next 5 minutes.

As the GBM assumption has already been verified for the level of drowsiness, it was possible to use System 3 to compute the risk for the next 5 minutes. Thus $$t_{stop} = 5, T_{sampling} = \frac{1}{3},$$

y=9, $1_{window}$=42 (meaning that the whole signal is used). The key functions are shown in FIGS. 21 and 22.

Figure 21:
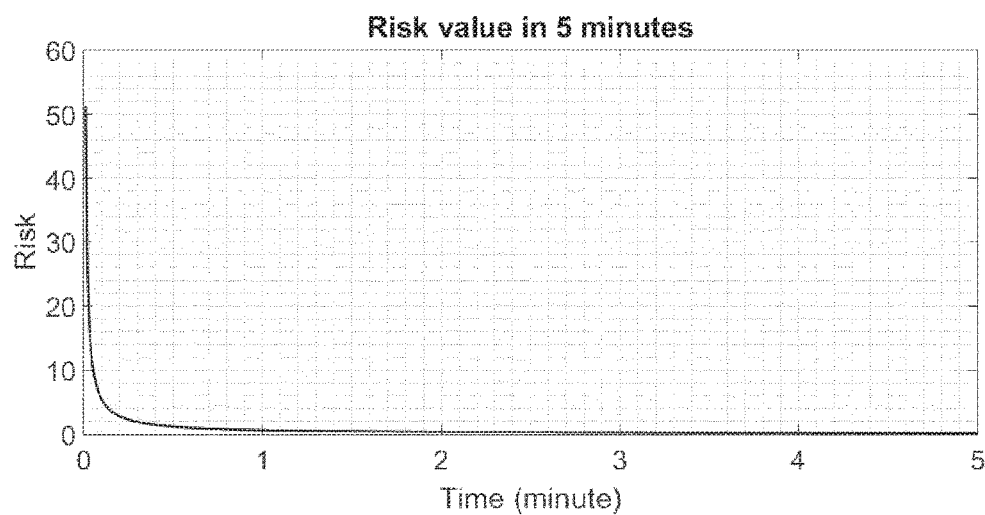
FIG. 21 shows an output from prediction device according to System 3 in Case B (corresponding to afternoon, with average LoD) for input shown in FIG. 20.

FIG. 21 represents the risk function (or signal) for the next 5 minutes. The function shown exhibits has all the necessary characteristics for a risk function. As one can see, the risk that the level of drowsiness passes through 9 for the next 30 seconds is extremely high; then it decreases very fast and it remains the same for the next 4 minutes and one-half. Because the value of the level of drowsiness is initially very close to 9, the risk of "failure" should be extremely high for the next few seconds. But if the person survived from that tough period, then the risk of his(/her) failure will decrease due to the hardiness. As already observed, this is in a sense a mathematical formulation of something quite natural: if a person or the subject of a study is able to survive in a tough condition with a very high risk of failure, then the risk of his failure should be decreased in time due to his hardiness if all the other parameters remained the same.

Figure 22:
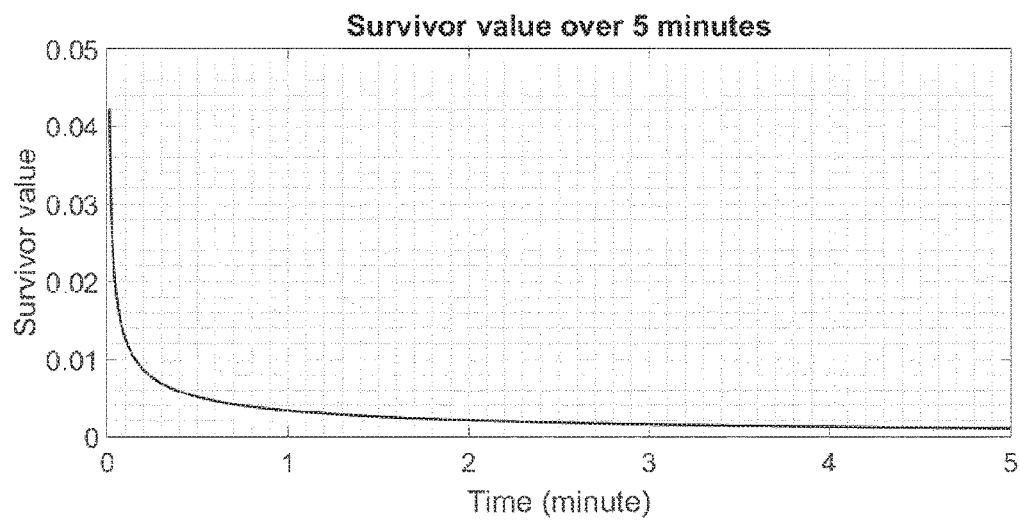
FIG. 22 shows an output from prediction device according to System 4 in Case B (corresponding to afternoon, with average LoD) for input shown in FIG. 20.

FIG. 22 represents the survivor function (or signal) for the next 5 minutes. It has all characteristics for a survivor function. As one can see, the probability that the level of drowsiness doesn't pass through 9 is very low even from the beginning. Because the value of the level of drowsiness is initially close to 9, the risk of failure should be extremely high for the next few seconds.

Comparison with More Traditional Approaches to Prediction

This section provides a comparison between (1) the approach considered in this work, where it is assumed that the input is a GBM random process, and (2) more traditional approaches, where it is assumed that the input is a moving average (MA) random process, or an autoregressive (AR) random process, or an autoregressive moving average modeling (ARMA) random process, or similar traditional random processes.

The corresponding techniques allow one to estimate the future values of a signal as a linear combination of previous (and known) values of the signal, typically in a window. Here too, the window slides. This means that one can view the prediction process as being modeled via a linear-time invariant (LTI) system. There are basically two approaches. The output is modeled as an LTI filter fed either with a unit impulse or with zero-mean, unit-variance white noise (WN). In the case of the impulse, the approach is purely deterministic, whereas in the case of the WN, the approach is random/stochastic. In fact, for each deterministic approach, there is generally one corresponding random/stochastic approach.

Figure 23:
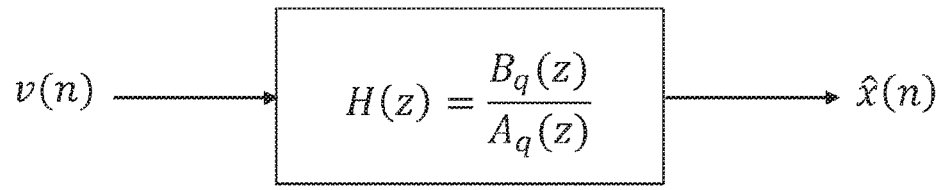
FIG. 23 shows a block diagram illustrating the modeling of discrete-time AR, MA, and ARMA random processes, where H(z) is the discrete-time system function.

In summary, the goal of all these methods is to model a given signal x(n) as the response of a linear shift-invariant filter to an input v(n), as shown in FIG. 23.

The goal is to find a filter with discrete-time transfer function H(z) (a z-transform) and input v(n) that make the output 2(n) as close as possible to x(n). x(n) can be deterministic or stochastic, which leads to two distinct categories of approaches.

The first category correspond to deterministic approaches, which include least square error methods, Padé approximation, Prony's method, Shank's method, all pole method, and linear prediction.

The second category corresponds to stochastic approaches, which include moving average (MA) modeling, autoregressive (AR) modeling, and autoregressive moving average (ARMA) modeling.

The difference between the approaches in these two categories is as follows. In all cases, one assumes that the input x(n) of interest (e.g. the level of drowsiness) is known over some interval of time that may or may not be contiguous. For simplicity of explanation, it is assumed that the input x(n) is known over some window. As indicated above, in all cases, one attempts to model the signal via the output of an LTI system. The main difference between the two types of approaches is that this "model" LTI system is fed with a unit impulse in the deterministic case, and with a zero-mean, unit variance white noise (WN) in the stochastic case. In all cases, the model LTI system is obtained by trying to best approximate the known part of x(n) with the response of the filter. The optimization criterion is often one of least-mean-square approximation. The difference between the two categories of approaches precisely lies in this modeling. In the category of deterministic approaches, the modeling is done (not surprisingly) deterministically, whereas in the stochastic approaches, it is done (not surprisingly) stochastically, i.e. by doing things in an ensemble-average fashion. But, in either case, one ends up with an LTI filter with a number of coefficients. The order of the filters depends upon how many values of x(n) are known, i.e. on the length of the window.

Once again, all these method attempt to predict the whole signal x(n) based on past value of x(n), typically in a window ending at the present time. All they can do is to determine an approximate model of the signal, and more specifically for the model LTI system. It is this model that is used to predict future values of x(n). For example, if n corresponds to the present time, these approaches allow one to predict the values of x(.) at n+1, n+2, etc.

Figure 24:
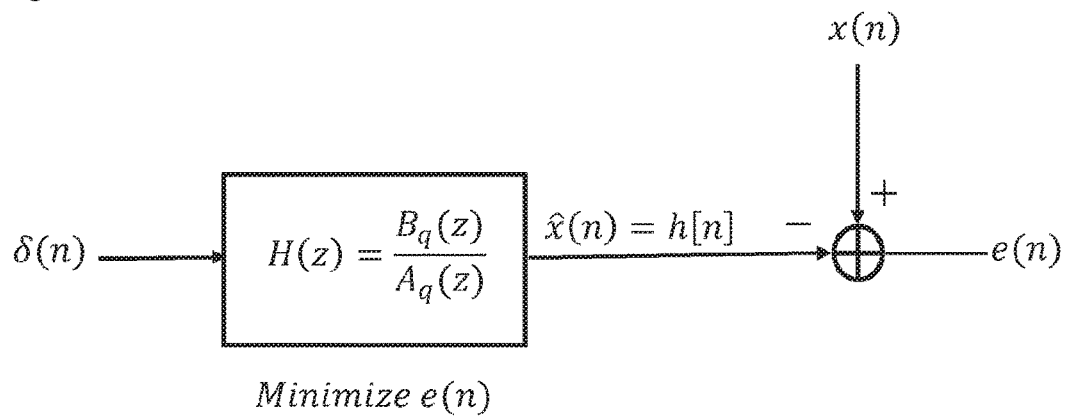
FIG. 24 shows a deterministic modeling, where the input of the filter H(z) is a unit impulse Impulse $\delta(n)$, and where the filter is designed so that its output matches as closely as possible the desired signal x(n).
Figure 25:
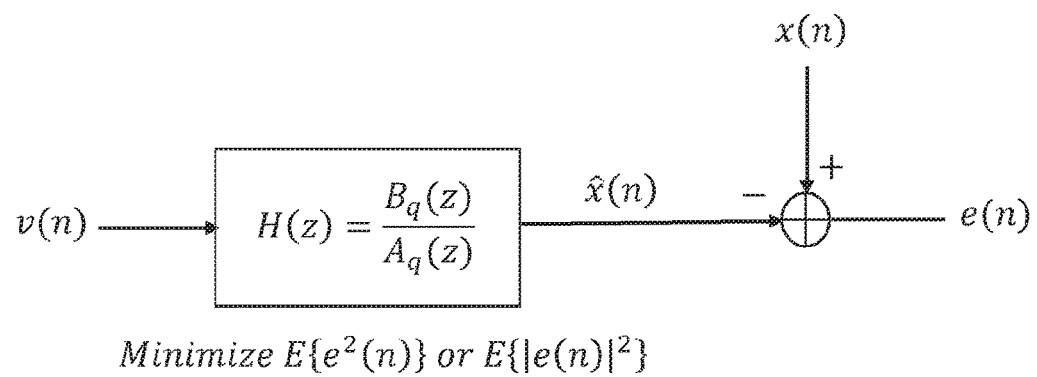
FIG. 25 shows a random/stochastic modeling, where the input to the filter H(z) is a unit variance white noise v(n), and where the filter is designed so that its output matches as closely as possible the desired x(n) in some statistical sense, usually in the mean-square error sense.

The set-ups for the methods in the first (i.e. deterministic) category and in the second (i.e. stochastic) category are shown in FIGS. 24 and 25, respectively.

The deterministic approaches (thus in the first category) are designed to model deterministic signals. Clearly, this is not ideal for the typical applications of the present invention, where it is desired to have prediction systems able to function properly in dynamic environments, i.e. in stochastic conditions. Of course, one might argue that any realization of a random process is a deterministic signal, so that the deterministic approaches are applicable.

It is even doubtful that the signal of interest, such as the level of drowsiness and the PERCLOS obey the stochastic models, such as, e.g. the AR, MA, or ARMA models.

However, even if one can properly predict the future values of the signal of interest, there is still a long way to go to get solid statistics such as a probability or a statistics such as an estimate of a mean. To get such statistical values, on would need to have recourse to Monte-Carlo simulations. Furthermore, the exercise would need to be repeated for each position of the sliding window. In addition, one should keep in mind that one may want to get the predictions in real time.

By contrast, in the case of the GBM random process model as in the present invention, closed form formulas are used to give such probabilities and expectations (i.e. statistical moments), etc. once the three parameters of the GBM random process model have been estimated. Furthermore, there is no problem in re-estimating these parameters in real time as the window slides.

Therefore, even without carrying out simulations, it is clear that the prediction approaches based on GBM random process modeling have significant advantages on prediction approaches based on (potentially questionable) AR, MA, and ARMA random process modeling.

Figure 26:
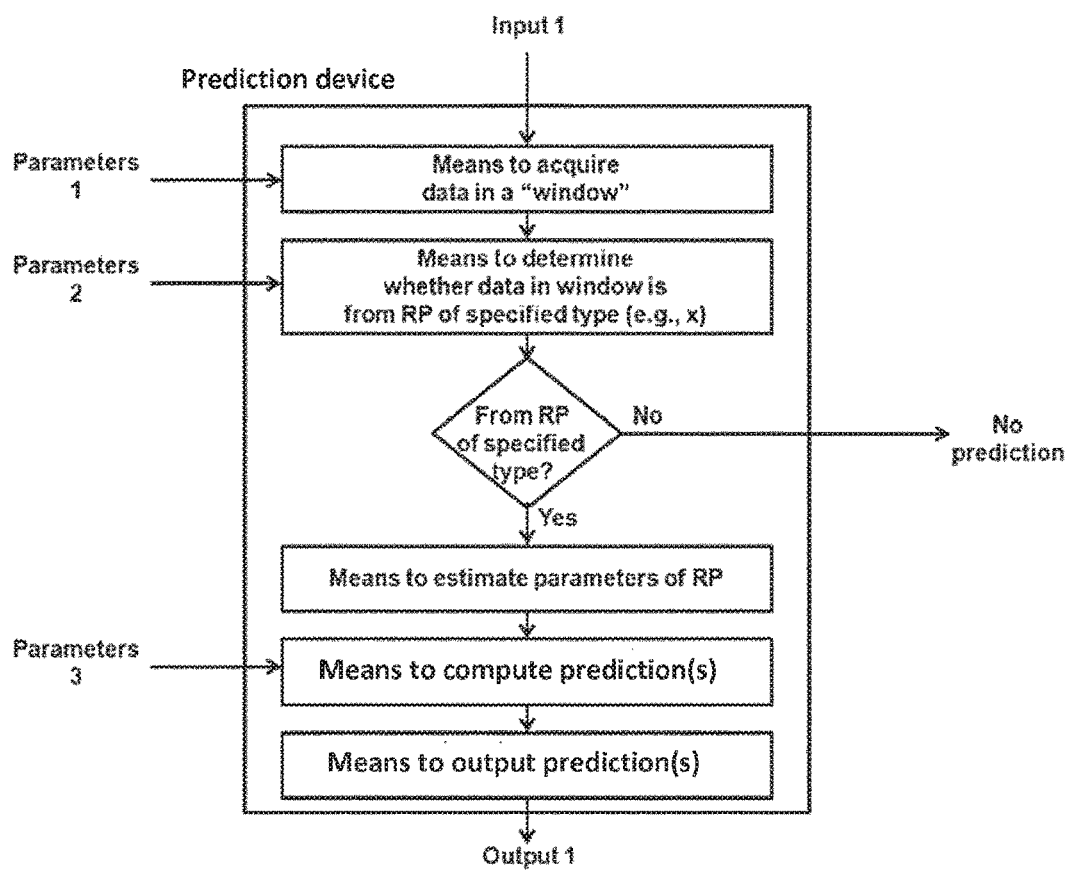
FIG. 26 shows an example of a flowchart of the prediction device according to the invention.
Figure 27:
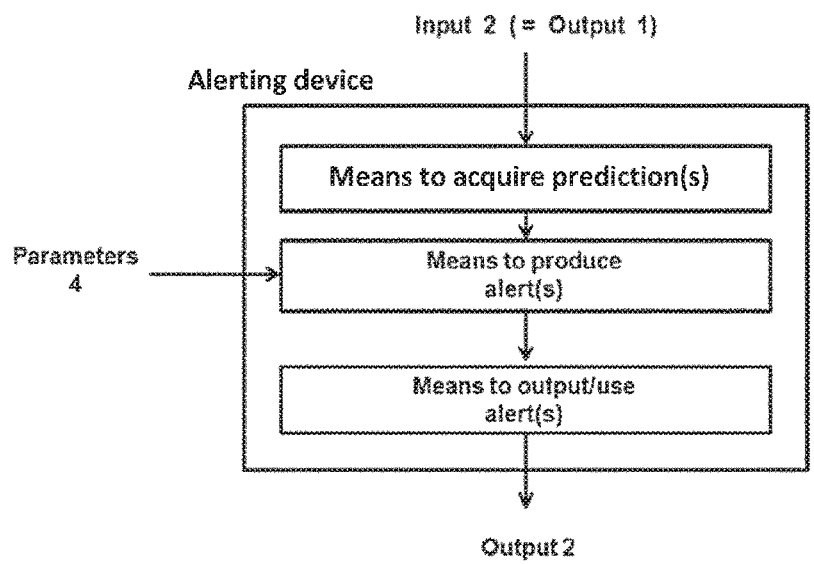
FIG. 27 shows an example of a flowchart of an alerting device using the prediction device according to the invention.
Figure 28:
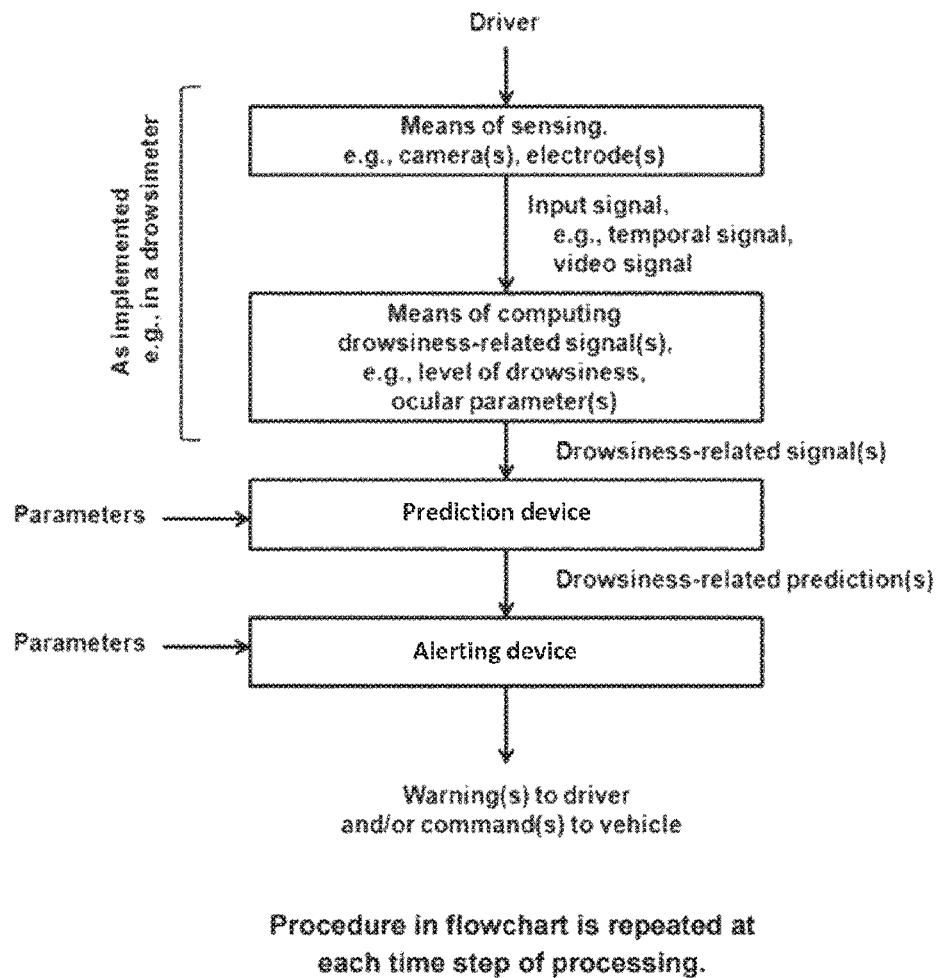
FIG. 28 shows an example of a flowchart of a device comprising the prediction device and the alerting device for the application of vehicle driving.

FIGS. 26, 27, and 28 show flowcharts further describing and illustrating the invention.

The invention claimed is:

1. A real time prediction device comprising
a means to acquire data from inside or outside a human being for one or more time periods in the past to obtain an acquired data set, wherein the data is a level of drowsiness or an ocular parameter indicative for drowsiness,
a computer means configured to model the acquired data set as a geometric Brownian motion (GBM) random process model or an Ito process (IP) random process model to obtain a fitted random process model,
a computer means configured to predict in real time a state of drowsiness of the human being using the fitted random process model to obtain a predicted state of drowsiness of the human being, and
an output for processed data or the predicted state.

2. The prediction device according to claim 1, wherein the means to model the acquired data set is a means to model the acquired data set as a geometric Brownian motion (GBM).

3. The prediction device according to claim 1, wherein the acquired data set comprises a temporal signal or spatial-temporal signal.

4. The prediction device according to claim 1, wherein the device further comprises a means to alert when the predicted state of the human being reaches one or more reference levels or is within reference bands.

5. The prediction device according to claim 1, wherein the data as issued by the human being is one or more of the following data: level of drowsiness (LoD), average of reaction time, average of eyelid closure speed, average of eyelid opening speed, average of closed eyes duration, and/or percentage of eye closure.

6. The prediction device according to claim 5, wherein the data as issued by the human being comprises the level of drowsiness (LoD) and the means to acquire the data is based on polysomnography (PSG) or photooculography (POG).

7. The prediction device according to claim 1, wherein the predicted state of the human being is provided by one or more mathematical expressions describing the mathematical expectation of the time from the present moment at which the data as issued by the human being becomes greater than a specified reference level.

8. The prediction device according to claim 1, wherein the predicted state of the human being is provided by one or more mathematical expressions describing the probability that the value of the data as issued by the human being is between two specified reference levels for a time tin the future.

9. The prediction device according to claim 1, wherein the predicted state of the human being is provided by one or more mathematical expressions describing a risk that the data as issued by the human being reaches and becomes greater than a specified reference level for a time tin the future.

10. A real time prediction device comprising
a means to acquire data from inside or outside a human being for one or more time periods in the past to obtain an acquired data set, wherein the data is a level of drowsiness or an ocular parameter indicative for drowsiness,
a computer means configured to model the acquired data set as a geometric Brownian motion (GBM) random process model or an Ito process (IP) random process model to obtain a fitted random process model,
a computer means configured to predict in real time a state of drowsiness of the human being using the fitted random process model to obtain a predicted state of drowsiness of the human being, and
an output for processed data or the predicted state;
wherein the predicted state of the human being is provided by one or more mathematical expressions describing a risk that the data as issued by the human being reaches and becomes greater than a specified reference level for a time tin the future; and
wherein the mathematical expressions describing a risk are based on a survival analysis and wherein the means to model the acquired data set is a means to model the acquired data set as a geometric Brownian motion (GBM) random process and wherein the device comprises computer means configured to obtain the mathematical function describing the risk function for a geometric Brownian motion (GBM) random process model by performing the following steps:

Step 1: find the survivor function for a GBM random process model with initial state X(0)=0;

Step 2: perform a change of variable in the survivor function obtained in "Step 1" to obtain a survivor function for a GBM random process model with initial state Y(0)=Y_1, wherein Y(0) is the initial state and Y_1∈ℝ⁺; and Step 3: convert the survivor function to the risk function using relation:

$$r(t) = -\left(\frac{dS(t)/dt}{S(t)}\right),$$

wherein t is time, r(t) is the risk function, X(t) is the data issued by the human being, S(t) is a survivor function, and dS(t)/dt the time derivative of the survivor function S(t).

11. The prediction device according to claim 1, wherein the predicted state of the human being is provided by one or more mathematical expressions or procedures describing the probability that the data as issued by the human being reaches and becomes greater than a specified reference level for a time t in the future.

12. The prediction device according to claim 1, wherein the predicted state of the human being is provided by one or more mathematical expressions describing the probability that the data as issued by the human being remains lower than a specified reference level at all times greater than t for a time t in the future.

13. A prediction device comprising
a means to acquire data from inside or outside a human being for one or more time periods in the past to obtain an acquired data set, wherein the data is a level of drowsiness or an ocular parameter indicative for drowsiness,
a computer means configured to model the acquired data set as a geometric Brownian motion (GBM) random process model or an Ito process (IP) random process model to obtain a fitted random process model, and
a computer means configured to predict in real time a state of drowsiness of the human being using the fitted random process model to obtain a predicted state of drowsiness of the human being, and
an output for processed data or the predicted state;
wherein the device further comprises at least two means to predict the level of drowsiness of the human being based on the same or different acquired data sets and means to generate a combined predicted state of the human being based on the predicted state of the human being.

14. The prediction device according to claim 5 in combination with a means of transportation including a driver as the human being.

15. A method for a real time prediction for drowsiness wherein a human being issues a level of drowsiness or an ocular parameter indicative for drowsiness as data and wherein the method comprises the following steps,
(a) acquiring the data by a data acquiring means from inside or outside the human being for one or more time periods located in a time interval comprised from a moment in the past to the present moment to obtain an acquired data set,
(b) modeling the acquired data set by a first computer means, wherein the acquired state set is modelled as a geometric Brownian motion (GBM) random process model or an Ito process (IP) random process model to obtain a fitted random process model,
(c) predicting a real time prediction of a state of drowsiness of the human being by a second computer means using the fitted random process model, and
(d) outputting processed data or the predicted state through an output device.

16. The method according to claim 15, wherein in step (b) the acquired data set is modelled as a geometric Brownian motion (GBM).

17. The method according to claim 15, wherein the method comprises a step (d) wherein an alert is activated when the predicted state of drowsiness is equal to one or more reference levels or is within a reference band.

18. The method according to claim 15, wherein the level of drowsiness or an ocular parameter indicative for drowsiness data as issued by the human being is one or more of the following data: level of drowsiness (LoD), average of reaction time, average of eyelid closure speed, average of eyelid opening speed, average of closed eyes duration, and/or percentage of eye closure.

19. The method according to claim 18, wherein in step (a) the level of drowsiness (LoD) is acquired via polysomnography (PSG) or via photooculography (POG).

20. The method according to claim 16, wherein the predicted state of the human being is provided by one or more mathematical expressions or procedures describing the risk that the data as issued by the human being reaches and becomes greater than a specified reference level for a time t in the future,
wherein the mathematical expressions or procedures describing the risk are based on a survival analysis, wherein the device comprises means to obtain the mathematical function describing the risk function for a geometric Brownian (GBM) random process model by performing the following steps:

Step 1: find the survivor function for a GBM random process model with initial state X(0)=0;

Step 2: perform a change of variable in the survivor function obtained in "Step 1" to obtain a survivor function for a GBM random process model with initial state Y(0)=Y_1, wherein Y(0) is the initial state and Y_1∈ℝ⁺; and Step 3: convert the survivor function to the risk function using relation:

$$r(t) = -\left(\frac{dS(t)/dt}{S(t)}\right),$$

wherein t is time, r(t) is the risk function, X(t) is the data issued by the human being, S(t) is a survivor function, and dS(t)/dt the time derivative of the survivor function S(t).

* * * * *